(12) United States Patent
Asik et al.

(10) Patent No.: US 11,318,104 B2
(45) Date of Patent: *May 3, 2022

(54) MICROCAPSULE AND PRODUCTION METHOD THEREOF

(71) Applicants: Mehmet Dogan Asik, Ankara (TR); Murat Bozkurt, Ankara (TR)

(72) Inventors: Mehmet Dogan Asik, Ankara (TR); Murat Bozkurt, Ankara (TR)

( * ) Notice: Subject to any disclaimer, the term of this patent is extended or adjusted under 35 U.S.C. 154(b) by 508 days.

This patent is subject to a terminal disclaimer.

(21) Appl. No.: 16/323,993

(22) PCT Filed: Aug. 9, 2017

(86) PCT No.: PCT/TR2017/050382
§ 371 (c)(1),
(2) Date: Feb. 7, 2019

(87) PCT Pub. No.: WO2018/070959
PCT Pub. Date: Apr. 19, 2018

(65) Prior Publication Data
US 2021/0023016 A1    Jan. 28, 2021

(30) Foreign Application Priority Data
Aug. 11, 2016  (TR) .................. 2016/11332

(51) Int. Cl.
| | | |
|---|---|---|
| *A61K 9/50* | (2006.01) | |
| *A61K 47/68* | (2017.01) | |
| *C12N 5/00* | (2006.01) | |
| *A61L 27/54* | (2006.01) | |
| *B01J 13/22* | (2006.01) | |
| *A61K 35/12* | (2015.01) | |
| *B01J 13/14* | (2006.01) | |
| *B82Y 30/00* | (2011.01) | |
| *B32B 9/00* | (2006.01) | |

(52) U.S. Cl.
CPC .......... *A61K 9/5042* (2013.01); *A61K 9/5089* (2013.01); *A61K 35/12* (2013.01); *A61K 47/6843* (2017.08); *A61L 27/54* (2013.01); *B01J 13/14* (2013.01); *B01J 13/22* (2013.01); *C12N 5/0012* (2013.01); *A61K 2035/128* (2013.01); *A61L 2300/622* (2013.01); *A61L 2300/64* (2013.01); *B32B 9/00* (2013.01); *B82Y 30/00* (2013.01); *C12N 2533/74* (2013.01)

(58) Field of Classification Search
None
See application file for complete search history.

(56) References Cited

U.S. PATENT DOCUMENTS

| | | | |
|---|---|---|---|
| 5,238,714 A | 8/1993 | Wallace et al. | |
| 8,518,682 B2 * | 8/2013 | Freyman | A61P 3/00 435/177 |
| 2009/0286278 A1 | 11/2009 | Yu et al. | |
| 2011/0221083 A1 | 9/2011 | Laulicht et al. | |
| 2012/0270295 A1 | 10/2012 | Choo et al. | |
| 2016/0030360 A1 | 2/2016 | Vegas et al. | |
| 2019/0381211 A1 * | 12/2019 | Asik | C12N 5/0012 |

FOREIGN PATENT DOCUMENTS

DE    102013108453 A1    2/2015

OTHER PUBLICATIONS

Branco da Cunha et al., "Influence of the stiffness of three-dimensional alginate/collagen-I interpenetrating networks on fibroblast biology", Biomaterials 35: 8927-8936 (2014) (Year: 2014).*
International Search Report for PCT/TR2017/050382, dated May 3, 2018.
International Preliminary Report on Patentability for PCT/TR2017/050382, dated Feb. 12, 2019.

* cited by examiner

*Primary Examiner* — Anand U Desai
(74) *Attorney, Agent, or Firm* — Egbert, McDaniel & Swartz, PLLC

(57) ABSTRACT

Disclosed is a microcapsule which is used in tissue regeneration, which may be specifically directed to the damaged tissues, and which forms an extracellular matrix-like structure at a certain point and thus allows cell proliferation, and to the production method of such microcapsule.

8 Claims, 5 Drawing Sheets

MICROCAPSULE AND PRODUCTION METHOD THEREOF

TECHNICAL FIELD

The present invention relates to a microcapsule which is used in tissue regeneration, which may be specifically directed to the damaged tissues, and which forms an extracellular matrix-like structure at a certain point and thus allows cell proliferation, and to the production method of such microcapsule.

PRIOR ART

The science field aiming at functionalizing the tissues which are damaged due to any reason or which are not structurally and functionally sufficient is tissue engineering. In other words, tissue engineering is a science field which aims to form functional and healthy tissues and organs instead of diseased or dead tissues. In the process or forming a single tissue or organ, it is required to identify suitable tissue scaffolds, cell sources, and signals. In this cellular treatment approach, after the isolated cells are cultured on scaffolds designed in a similar way to three-dimensional extracellular matrix molecules in vitro, they are re-differentiated and proliferated under special conditions, and then the thus formed new tissue-like hybrid structures are again transplanted to the body.

First, the cells collected from a small tissue sample are proliferated in laboratory environment. Afterwards, they are combined with tissue scaffolds having a functionality to form a tissue and a hybrid system is thus formed in tissue engineering. Here, the tissue scaffold serves as a temporary host used by the tissue to be delivered to the body until it adjust to the body. That is, since the tissue scaffold has a biodegradable structure, it starts to degrade some time after being delivered to the body. Finally, the tissue scaffold disappears and the tissue starts to serve for its function at maximum performance as required.

In preparation of the tissue scaffold, nanotechnology plays an important role not only in the development of materials but also in making structures with the desired genetic, topographical, and functional properties of these materials. With nanoscale fabrication techniques, the knowledge on nanosized cellular behaviors and tissue organization is increasing day by day. In some of these systems, the natural structures of which are mimicked in the best way possible and the tissue scaffolds of which are realized with nanofabrication techniques, collagen fibers are used.

Cell encapsulation is the process in which the cell is enclosed in a polymeric semipermeable membrane which allows dual passage such that the entry of such molecules as oxygen, nutrient, and growth factor which are required for the cell metabolism and the exit of waste products and healing proteins will be allowed.

The main goal of the cell encapsulation technology is to overcome the existing rejection incidences in transplanted tissues in tissue engineering and to reduce long-term immunosuppressive drug use after transplantation.

Cell encapsulation technology has been known for many years in the state of the art. However, open surgery is needed so as to introduce the encapsulated cell into the body. Further, the encapsulated cells injected to the body are not targeted to any point. There exists neither a microcapsule which comprises living cells therein and thus may be targeted to a site of preference nor the production method of such a microcapsule.

In the state of the art, the U.S. Patent Application No. US2009286278 A1 discloses cell encapsulation, particularly living cell encapsulation into multi-layer polymeric membranes. The multi-layered microcapsule has an inner layer of biopolymer and an outer shell of polymer. In this invention, although the cell is encapsulated in a multi-layer polymeric structure, the encapsulated cell lacks the property of being targeted to a given point.

Another document in the state of the art is the U.S. Patent Application No. US5238714 A1, wherein a method of preparing microcapsules suitable for encapsulation of therapeutic and diagnostic agents is disclosed. The capsular coats are prepared from biodegradable polymers. This invention also comprises microcapsules obtained from polymers conjugated to an amino acid. With this invention, a microcapsule loaded with a drug is targeted to a specific organ or cell. The present invention, however, differs from cell encapsulation and it relates to living cell encapsulation, targeting a microcapsule having living cells to a specific point, and to the production method of such microcapsules.

And another document in the state of the art is the U.S. Patent Application No. US2012270295 A1, wherein a method for encapsulating living cells and labels, as well as encapsulated labelled cells and kits for performing such encapsulation is disclosed. This invention describes labelling method of cells and cell groups. Thanks to this method, microcapsules comprising one or more labels are obtained. Therefore, a microcapsule having a living cell and a label is obtained. However, this invention does not describe any method of targeting a microcapsule having living cells therein.

In the state of the art, there exist no microcapsule which carries living cells and may be targeted to the damaged site desired to be treated thanks to the living cells that it carries, which forms a structure at the damaged site to which it is targeted and allows cell proliferation at this site, and which eliminates the need for open surgery, nor a production method for such microcapsules.

Objects of the Invention

The object of the present invention is to provide a microcapsule which may be directed to a preferred target and which comprises living cells, as well as a microcapsule production method.

An object of the present invention is to provide a microcapsule and microcapsule production method which eliminate the need for open surgery in order to be able to treat damaged tissues.

Another object of the invention is to provide a microcapsule and microcapsule production method to be used for forming a structure which may be directly targeted to the damaged tissue and having extracellular matrix properties in order to eliminate the damage.

And another object of the invention is to provide a microcapsule and microcapsule production method which, by forming a structure having extracellular matrix properties, allow cell proliferation and tissue regeneration.

BRIEF DESCRIPTION OF THE INVENTION

A microcapsule which has been developed in order to achieve the objects of the present invention and which has been defined in the first claim as well as in the other dependent claims comprises a living cell therein. A microcapsule is formed by various polymer layers coated onto the living cell. The characteristic of the microcapsule is that it encapsulates living cells and has a structure such that it can be targeted to the desired tissue along with these cells. First, the living cell is coated thereon with a polymer. The coated primary layer is a biodegradable polymer. Side groups are present on the primary layer. The side groups on the outer surface of the primary layer ensure that the second layer binds to the surface of the primary layer. The second layer is a polymer. The polymer to constitute the second layer is functionalized prior to binding to the microcapsule. Bridging factor is a molecule that will allow the formation of a bridge between two molecules, e.g. a protein, an amino acid sequence, a chemical molecule, and a DNA sequence. Later, the bridging factor is linked to the functionalized polymer by means of a binding molecule (linker). The bridging factor-bound secondary polymer is coated onto the primary layer. Afterwards, the outermost bridging factors bind the targeting factor and tissue formation/accumulation factor to the microcapsule by means of a bridge. Thus, a microcapsule structure with a cell therein and tissue formation/accumulation and targeting factors in the outermost surface thereof is formed.

In the microcapsule production method which has been developed in order to achieve the objects of the present invention and which has been defined in the first claim as well as in the other dependent claims, first the encapsulation of the cells is performed. The encapsulation of the living cell is performed with a polymer. The polymer used this embodiment of the invention is alginate. After the encapsulation process, the living cell becomes coated with the primary layer having side groups thereon, i.e. with alginate. Once the primary layer is formed, functionalization of the secondary polymer is performed. The functionalized polymer in this embodiment of the invention is chitosan. Subsequent to the functionalization process, avidin, which is selected as the bridging factor, is bound to the chitosan. Once these processes are completed, chitosan is coated onto the primary layer such that it will form the second layer. After the coating process, the targeting and tissue formation/accumulation factors are bound on the functionalized polymer; thus, the second layer and the microcapsule at the end of the process are obtained. In the preferred embodiment of the invention, targeting and tissue formation/accumulation factors are biotinylated antibodies.

DESCRIPTION OF THE SEVERAL VIEWS OF THE DRAWINGS

The microcapsule and the production method of this microcapsule, which have been developed for achieving the objects of the present invention, are illustrated in the accompanying drawings, in which.

Figure 1:
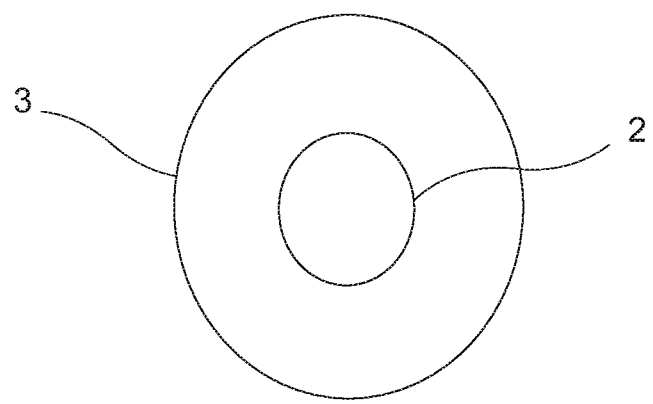
FIG. 1. Schematic view of the cell coated with the primary layer.
Figure 2:
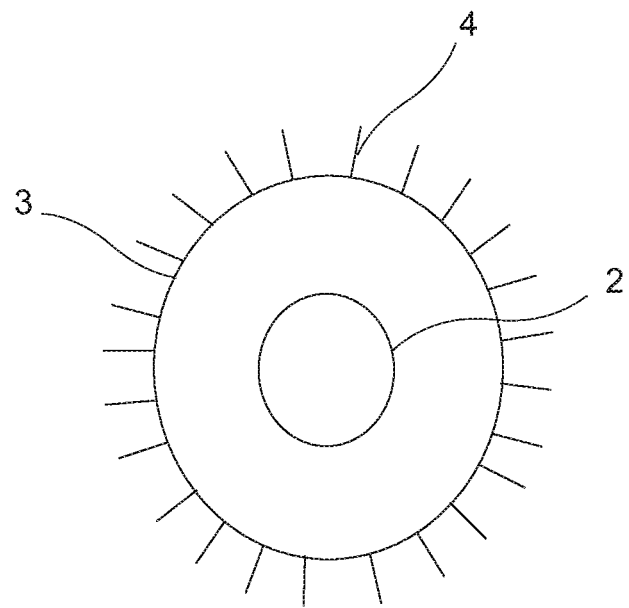
FIG. 2. Schematic view of the side groups bound on the primary layer.
Figure 3:
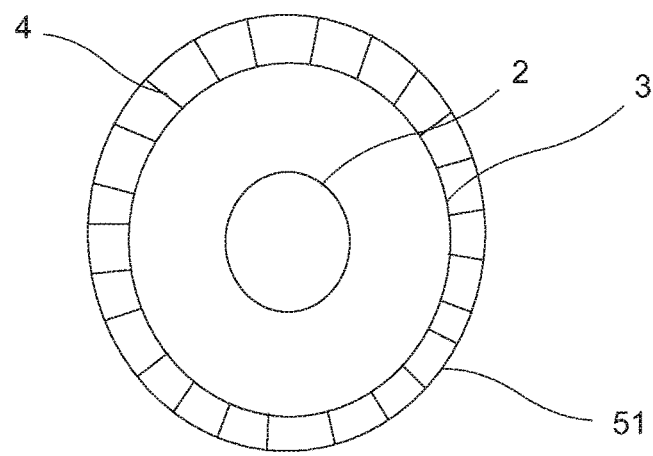
FIG. 3. Schematic view of the functionalized polymer bound to the primary layer and the side groups present on the primary layer.
Figure 4:
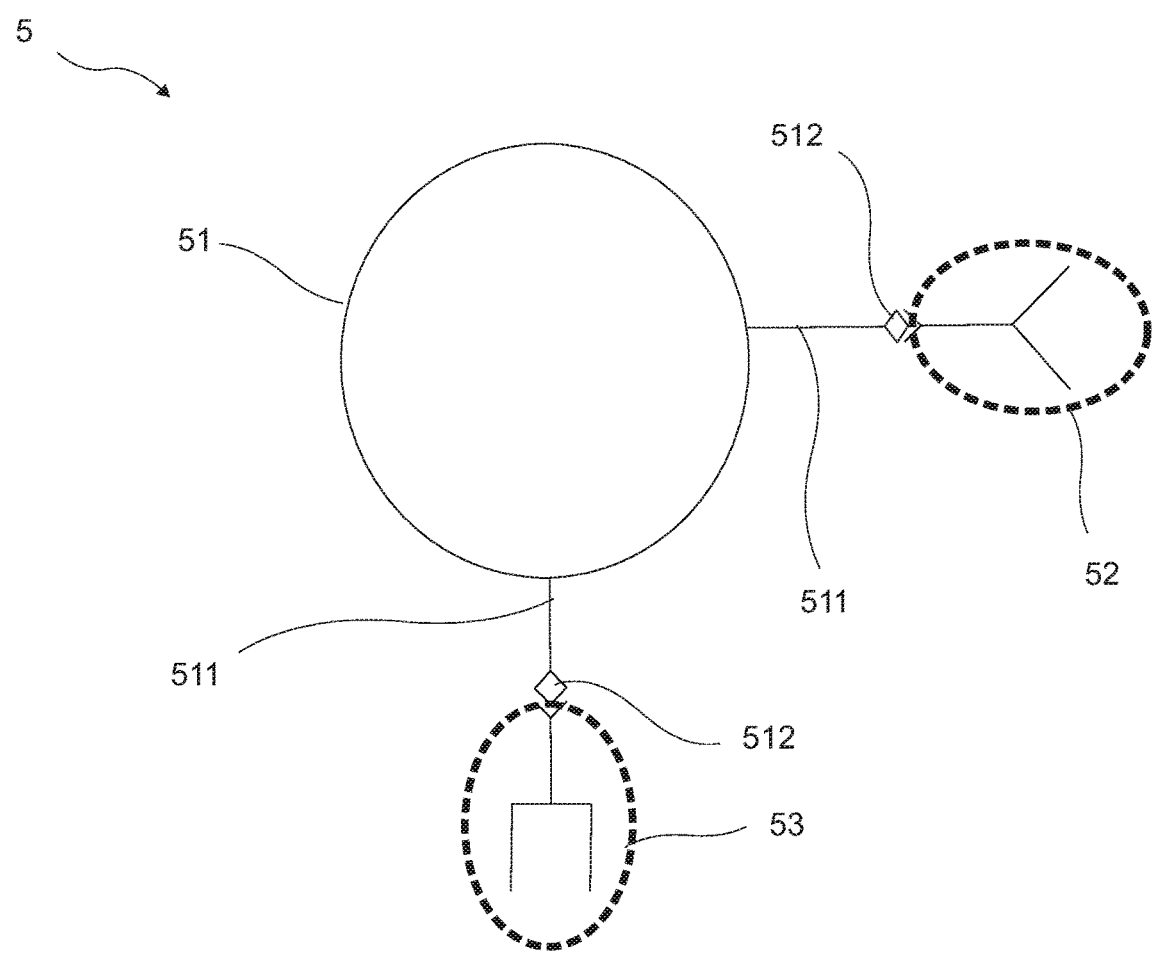
FIG. 4. Schematic view of the second layer.
Figure 5:
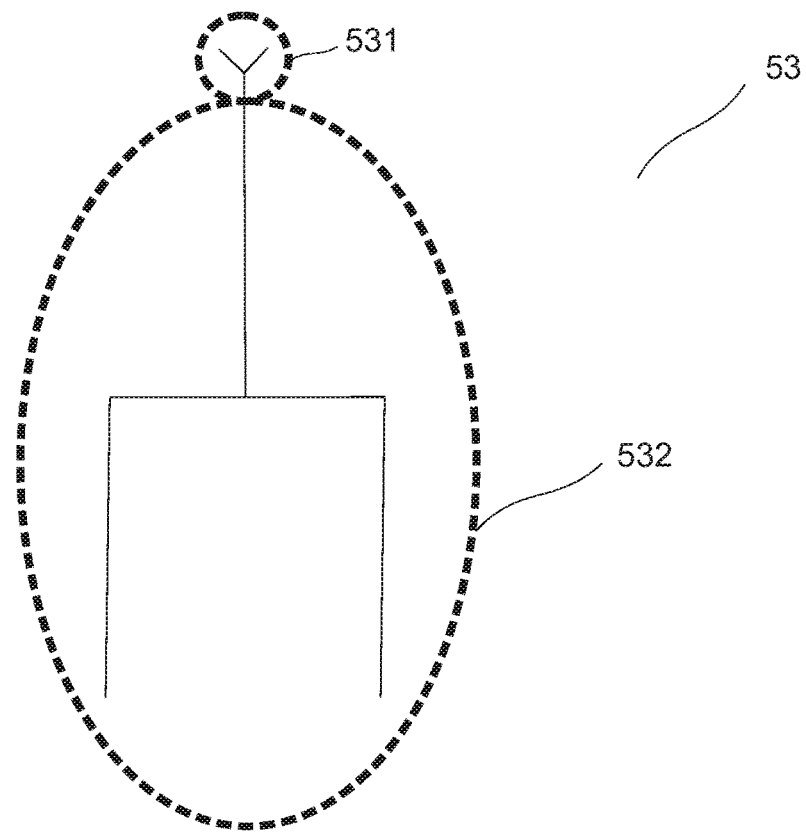
FIG. 5. Schematic view of the tissue formation/accumulation factor.
Figure 6:
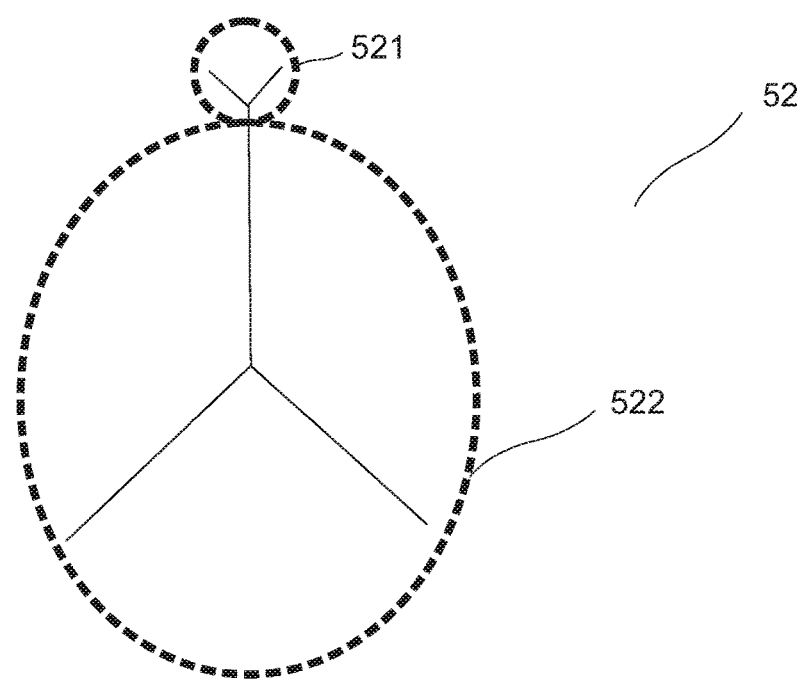
FIG. 6. Schematic view of the targeting factor.
Figure 7:
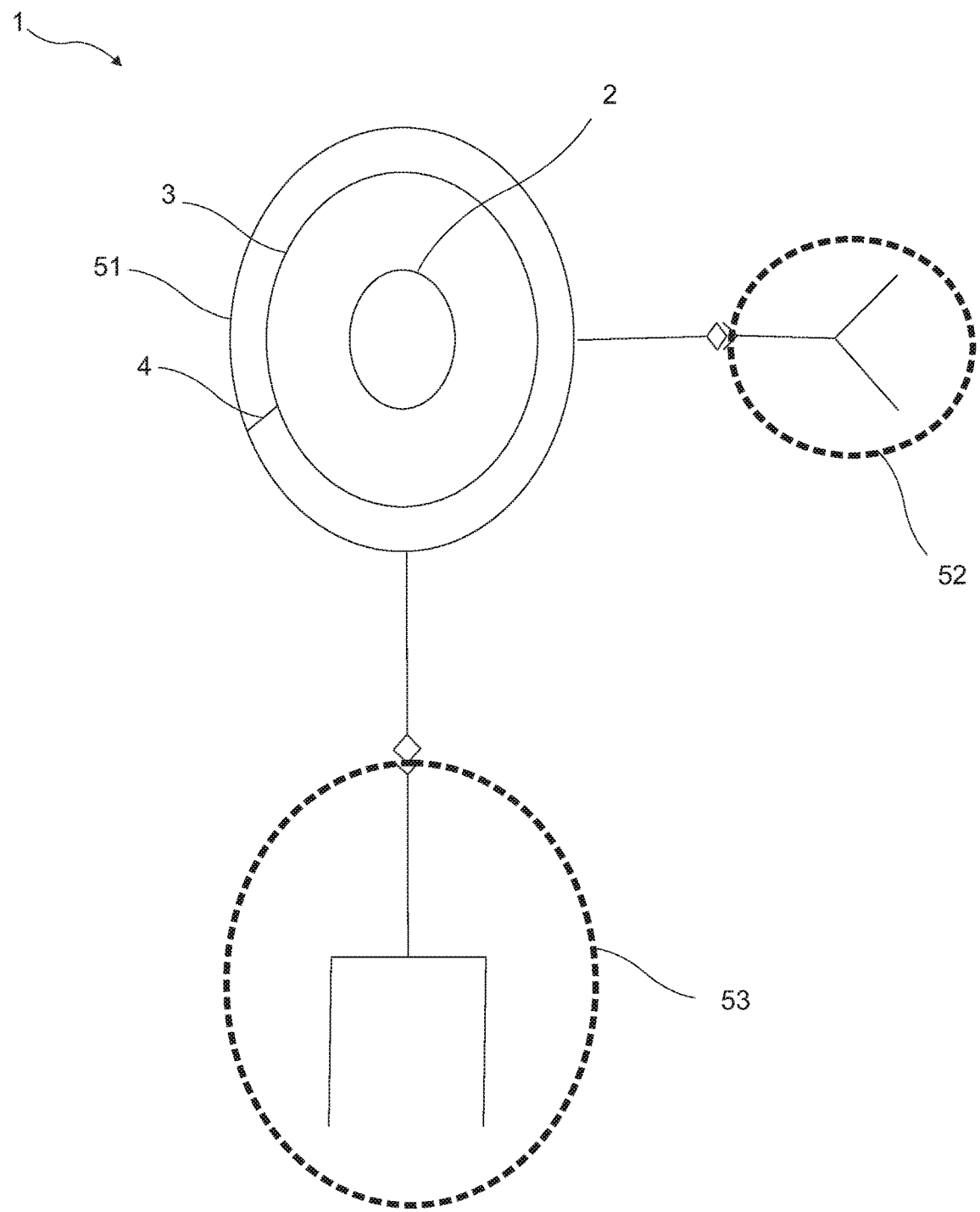
FIG. 7. Schematic view of the microcapsule.
Figure 8:
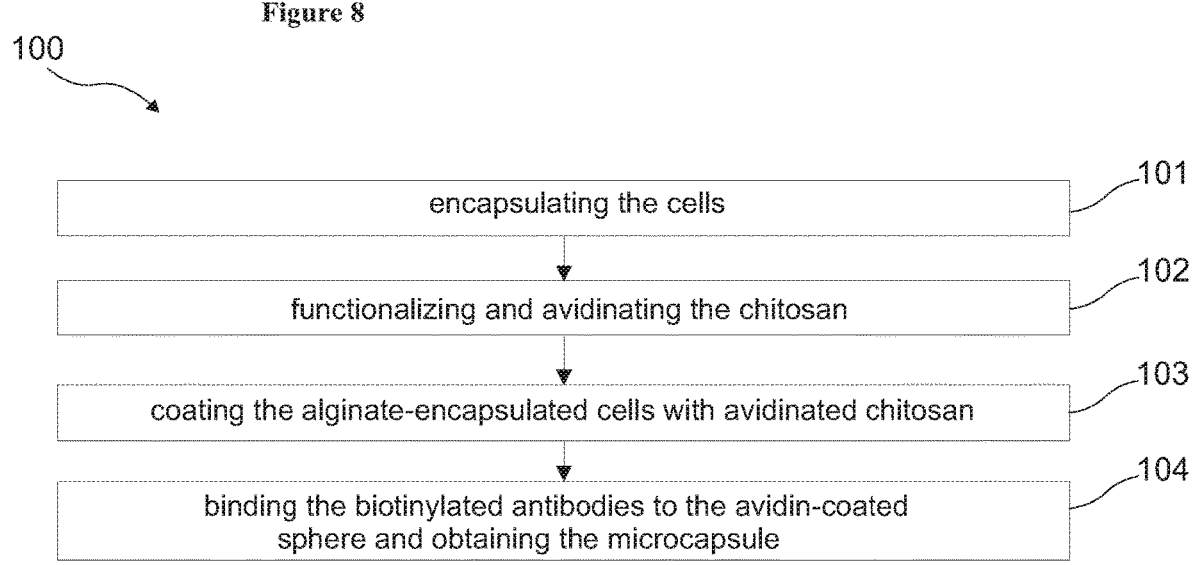
FIG. 8. Schematic view showing the steps of the microcapsule production method.

The parts in the drawings are enumerated individually and the reference numerals corresponding thereto are given below.
1. Microcapsule
2. Cell
3. Primary layer
4. Side group
5. Second layer
　51. Functionalized polymer
　　511. Binding molecule (linker)
　　512. Bridging factor
　52. Targeting factor
　　521. Targeting bridge factor
　　522. Targeting agent
　53. Tissue formation/accumulation factor
　　531. Tissue formation/accumulation bridge factor
　　532. Tissue formation/accumulation point
100. Microcapsule production method

DETAILED DESCRIPTION OF THE INVENTION

A microcapsule which is used in tissue regeneration, which may be specifically directed to the damaged tissues, and which forms an extracellular matrix-like structure at a certain point basically comprises:
- at least one living cell (2),
- at least one primary layer (3) enclosing the living cell (2),
- at least one and at least one type of side group (4) to which another layer to enclose the primary layer (3) is bound,
- at least one second layer (5) comprising at least one functionalized polymer (51), at least one and at least one type of targeting factor (52), and at least one enhancing tissue formation/accumulation factor (53),
- a functionalized polymer (51) which is coated onto the primary layer (3) and which has the property of being targeted,
- a targeting factor (52) present on the functionalized polymer (51) and allows targeting the damaged point, and
- a tissue formation/accumulation factor (53) which enhances the adhesion surface on the functionalized polymer (51).

In an embodiment of the invention, the microcapsule (1) comprises living cell. The cell (2) is the innermost element. Once the living cell (2) within the microcapsule (1) reaches the damaged site, it creates an additional coupling surface on the damaged site for the formation of a scaffold. The microcapsule (1) moves along with the cell (2).

In an embodiment of the invention, the cell (2) is coated with a primary layer (3). The primary layer (3) is a polymer chain. The primary layer (3) may be gelatin, elastin, cellulose, chitin, chitosan, carboxymethyl chitosan and chitosan derivatives, alginate, poly methyl methacrylate, all polyacrylamides, polyethylene, polylactic acid, polyglycolic acid, PLGA (polylactic-co-glycolic acid), polyethylene oxide, polyurethane, poly hydroxymethyl methacrylate, poly amino esters, and any type of crosslinkers thereof. In the preferred embodiment of the invention, the primary layer (3) is alginate. A circular capsule is formed around the cell (2) by crosslinking the primary layer (3) and the crosslinker. The primary layer (3) constitutes the first layer of the multi-layer structure of the microcapsule (1).

In an embodiment of the invention, the primary layer (3) is a biodegradable polymer.

In an embodiment of the invention, the primary layer (3) is provided thereon with more than one side groups (4). The side groups (4) are the structures allowing the second layer (5) to attach to the surface. The side groups (4) on the primary layer (3) may be identical or more than one type. The side groups (4) may be coupled to one another via physical and/or chemical interactions. The side groups (4) may be one or more of haloformyl, hydroxyl, aldehyde, alkyl, alkenyl, alkynyl, carboxamide, primary amine, secondary amine, tertiary amine, azide, azo, benzyl, carbonate ester, carboxylate, carboxyl, cyanate, thiocyanate, disulfide, ether, ester, halo, hydroperoxy, primary ketimine, secondary ketimine, primary amine, secondary amine, imide, isocyanide, isocyanate, isothiocyanate, carbonyl, nitrate, nitryl, nitrosooxy, nitro, nitroso, peroxy, phenyl, phosphino, phosphate, phosphono, pyridyl, sulfide, sulfo, sulfinyl, and sulfhydryl. In the preferred embodiment of the invention, the side groups (4) are carboxyl and amine groups. The side groups (4) allow the formation of a multi-layer structure.

In an embodiment of the invention, there exists a second layer (5). The second layer (5) is the structure that enables the microcapsule (1) to be targeted to the preferred point. The second layer (5) is a layer in which targeting factors (52) and tissue formation/accumulation factors (53) are present on the functionalized polymer (51). First, the polymer is functionalized in order to obtain the second layer (5). The functionalized polymer (51) may be gelatin, elastin, cellulose, chitin, chitosan, carboxymethyl chitosan and chitosan derivatives, alginate, poly methyl methacrylate, all polyacrylamides, polyethylene, polylactic acid, polyglycolic acid, PLGA (polylactic-co-glycolic acid), polyethylene oxide, polyurethane, poly hydroxymethyl methacrylate, poly amino esters, and any type of crosslinkers thereof. In this embodiment of the invention, the functionalized polymer (51) is chitosan. The functionalized polymer (51) is coupled to the bridging factor (512) by way of a binding molecule (511). The bridging factor (512) allows the targeting factor (52) and the tissue formation/accumulation factor (53) to adhere to the functionalized polymer (51) by means of a bridge. The bridging factor (512) on the functionalized polymer (51) forms these bridges by means of the targeting bridge factor (521) and the tissue formation/accumulation factor (53). In this embodiment of the invention, the functionalized polymer (51) is chitosan.

In an embodiment of the invention, there exists a targeting factor (52). The targeting factor (52) allows the microcapsule (1) to be targeted to the site to which it is desired to reach. The targeting factor (52) comprises a targeting bridge factor (521) and a targeting agent (522). The targeting bridge factor (521), along with the bridging factor (512), forms a bridge between the functionalized polymer (51) and the targeting agent (522). At one end of the targeting bridge factor (521) is the targeting agent (522). The targeting agent (522) may be a protein, amino acid sequence, an aptamer, a DNA sequence, a receptor, or an antibody. In the preferred embodiment of the invention, the microcapsule (1) is used in cartilage tissue regeneration and the targeting agent (522) is cartilage-specific antibody.

In an embodiment of the invention, there exists a tissue formation/accumulation factor (53). The tissue formation/accumulation factor (53) forms the points of coupling on the microcapsule (1). The tissue formation/accumulation factor (53) comprises a tissue formation/accumulation bridge factor (531) and a tissue formation/accumulation point (532). The tissue formation/accumulation bridge factor (531), along with the bridging factor (512), forms a bridge between the functionalized polymer (51) and the tissue formation/accumulation point (532). At one end of the tissue formation/accumulation bridge factor (531) is the tissue formation/accumulation point (532). The tissue formation/accumulation point (532) may be a protein, amino acid sequence, an aptamer, a DNA sequence, a receptor, or an antibody. In the preferred embodiment of the invention, the tissue formation/accumulation point (532) is a rhodopsin-specific antibody.

With the microcapsule (1) according to the present invention, the need for open surgery in damaged tissue treatment is eliminated. The microcapsule (1) having living cell (2) therein may be directed/targeted to the damaged site of preference. The microcapsule (1) targeted to the site of preference and reaching that site forms a structure having extracellular (2) matrix properties at the damaged site. With the thus formed structure having extracellular (2) matrix properties, the cells (2) are proliferated and the tissue is regenerated.

The microcapsule production method (100) which is used in tissue regeneration, which may be specifically directed to the damaged tissues, and which forms an extracellular (2) matrix-like structure at a certain point and thus allows cell (2) proliferation comprises the process steps of:

encapsulating the living cells (2) with a polymer, preferably alginate, and obtaining the primary layer (3) with side groups thereon (4) (101), functionalizing the polymer, preferably chitosan, and binding the bridging factor (512), preferably avidin, to the functionalized chitosan (102), coating the encapsulated cells (2) with the functionalized polymer (51) in order to form the second layer (5) (103), and obtaining the second layer (5) and the microcapsule (1) by binding, on the functionalized polymer (51), preferably the biotinylated targeting factor (52) and the tissue formation/accumulation factor (53) (104).

With the microcapsule production method (100) according to the invention, a microcapsule (1) which may be directed to a damaged site in the body and which carries living cell (2) is obtained.

In the microcapsule production method (100), first the step of encapsulating the living cells (2) with a polymer, preferably alginate, and obtaining the primary layer (3) with side groups thereon (4) (101) is performed. In this step, the CaCl2 dissolved in water and a low molecular weight sodium alginate polymer again dissolved in water are cross-linked. The chondrocytes proliferated in the cell (2) culture are added into the alginate solution and instilled into the CaCl2 solution. The cell (2) is thus coated with the primary layer (3).

Subsequent to the cell (2) encapsulation (101), the step of functionalizing the polymer, preferably chitosan, and binding the bridging factor (512), preferably avidin, to the functionalized chitosan (102) is performed. In this step, the chitosan is functionalized and avidinated. First of all, low molecular weight chitosan polymer is dissolved in acetic acid solution. And then, the ambient pH value is increased to the physiological pH range. Once the pH value is increased, chitosan is first treated with functionalizing agent, and then with avidin molecules. Avidin-bound chitosan polymer chains are washed with acetic acid solution at least once.

After the functionalization of the secondary polymer, preferably chitosan, and the binding of the bridge factor, preferably avidin (102), the encapsulated cells (2) are coated with a functionalized polymer (51) in order to form the second layer (5) thereof (103). Encapsulated cells (2) are washed with the preferred isotonic solution. In this embodiment of the invention, the cells (2) are washed with PBS (Phosphate Buffered Saline) buffer solution and transferred to the PBS solution. After washing, the avidin-bound chitosan polymers are brought to pH 4.5 and introduced into the PBS solution (pH 7.4) in which encapsulated cells (2) are present.

After the encapsulated cells (2) are coated with the functionalized polymer (51) in order to form the second layer (5) (103), the second layer (5) and the microcapsule (1) are obtained by binding, on the functionalized polymer (51), preferably the biotinylated targeting factor (52) and the tissue formation/accumulation factor (53) (104). The solution comprising therein biotinylated antibodies specific to the damaged cartilage, e.g. glycoprotein, 80 anti-GPNMB, anti-CD90/THY1, anti-GPCR, anti-S100A9, anti-CXCR4, and anti-periostin, is instilled into the solution in which the encapsulated cells (2) are present. Once the instillation is performed, it is kept for 0-24 hours at 30-45° C. The avidinated chitosan is also treated with biotinylated rhodopsin for 0-24 hours in a different environment.

In the production method (100) of a multi-layer microcapsule which can be targeted to the site of preference, first, the step of encapsulating the living cells (2) with a polymer, preferably alginate, and obtaining the primary layer (3) with side groups thereon (4) (101) is performed. After the primary layer (3) is obtained, the secondary polymer, preferably chitosan, is functionalized and the bridging factor (512), preferably avidin, is bound to the polymer, preferably chitosan (102). Later, the encapsulated cells (2) are coated with the functionalized polymer (51) in order to form the second layer (5) (103). Upon completion of the coating process, the second layer (5) and hence the microcapsule (1) are obtained by binding, to the functionalized polymer (51), the targeting factor (52) and the tissue formation/accumulation factor (53).

The invention claimed is:

1. A microcapsule production method (100) which is used in tissue regeneration, which may be specifically directed to damaged tissues, and which forms an extracellular matrix-like structure at a certain point and thus allows cell proliferation, characterized in comprising the process steps of:
    encapsulating living cells with a first biodegradable polymer having side groups consisting of one or more of haloformyl, hydroxyl, aldehyde, alkyl, alkenyl, alkynyl, carboxamide, primary amine, secondary amine, tertiary amine, azide, azo, benzyl, carbonate ester, carboxylate, carboxyl, cyanate, thiocyanate, disulfide, ether, ester, halo, hydroperoxy, primary ketimine, secondary ketimine, primary amine, secondary amine, imide, isocyanide, isocyanate, isothiocyanate, carbonyl, nitrate, nitryl, nitrosooxy, nitro, nitroso, peroxy, phenyl, phosphino, phosphate, phosphono, pyridyl, sulfide, sulfo, sulfinyl, and sulfhydryl, and obtaining a primary layer (101),
    functionalizing a second biodegradable polymer, and binding a bridging factor to the functionalized second biodegradable polymer (102), the second biodegradable polymer selected from the group consisting of: gelatin, elastin, cellulose, chitin, chitosan, carboxymethyl chitosan and chitosan derivatives, alginate, poly methyl methacrylate, all polyacrylamides, polyethylene, polylactic acid, polyglycolic acid, PLGA (polylactic-co-glycolic acid), polyethylene oxide, polyurethane, poly hydroxymethyl methacrylate, poly amino esters, and any type of crosslinkers thereof,
    during the process step of functionalizing the second biodegradable polymer and binding the bridge factor to the functionalized second biodegradable polymer (102), an ambient pH value is brought up to a physiological pH range,
    coating the encapsulated living cells with the functionalized second biodegradable polymer in order to form a second layer (103), and
    obtaining the second layer and a microcapsule by binding, on the functionalized second biodegradable polymer, a biotinylated targeting factor (52) and a tissue formation/accumulation point consisting of one of a protein, an amino acid sequence, an aptamer, a DNA sequence, a receptor, or an antibody (104).

2. The microcapsule production method (100) of claim 1, said first biodegradable polymer being alginate, wherein during the process step of encapsulating the living cells with a first biodegradable polymer, and obtaining a primary layer (101), $CaCl_2$ dissolved in water and low molecular weight sodium alginate polymer again dissolved in water are crosslinked and chondrocytes proliferated in the cell culture are added into the alginate solution and instilled into the $CaCl_2$ solution, and thus the cell is coated with the primary layer.

3. The microcapsule production method (100) of claim 1, said bridge factor being avidin and said second biodegradable polymer being chitosan, wherein during the process step of functionalizing the second biodegradable polymer and binding a bridge factor avidin, to the functionalized second biodegradable polymer (102), low molecular weight chitosan polymer is dissolved in acetic acid solution and after the pH value is increased, chitosan is first treated with the functionalizing agent and then with the avidin molecules.

4. The microcapsule production method (100) as in of claim 1, said bridge factor being avidin and said second biodegradable polymer being chitosan, wherein during the process step of functionalizing the second biodegradable polymer and binding the bridge factor to the functionalized second biodegradable polymer (102), avidin-bound chitosan polymer chains are washed with acetic acid solution at least once.

5. The microcapsule production method (100) of claim 1, said bridge factor being avidin and said second biodegradable polymer being chitosan, wherein during the process step of coating the encapsulated living cells with the functionalized second biodegradable polymer in order to form the second layer (103), such encapsulated living cells are washed with PBS (Phosphate buffered saline) buffer solution and transferred to the PBS solution and avidin-bound chitosan polymers are brought to a pH value of 4.5 and introduced into the PBS solution at pH 7.4 in which encapsulated living cells are present.

6. The microcapsule production method (100) of claim 1, wherein during the process step of obtaining the second layer (5) and the microcapsule (1) by binding, on the functionalized polymer (51), preferably the biotinylated targeting factor (52) and the tissue formation/accumulation factor (53) (104), the solution which comprises therein glycoprotein 180 anti-GP MB or anti-CD90/THY1 or anti-GPCR or anti-S100A9 or anti-CXCR4 or anti-periostin or biotinylated antibodies specific to the damaged cartilage is instilled into the solution in which encapsulated cells (2) are present.

7. The microcapsule production method (100) as in claim 6, characterized in that during the process step of obtaining the second layer (5) and the microcapsule (1) by binding, on the functionalized polymer (51), preferably the biotinylated targeting factor (52) and the tissue formation/accumulation factor (53) (104), after the instillation is performed, the solution comprising biotinylated antibodies which is instilled into the solution in which encapsulated cells (2) are present is kept for 0-24 hours at 30-45° C.

8. The microcapsule production method (100) as in claim 7, characterized in that during the process step of obtaining the second layer (5) and the microcapsule (1) by binding, on the functionalized polymer (51), preferably the biotinylated targeting factor (52) and the tissue formation/accumulation factor (53) (104), the avidinated chitosan is treated with the biotinylated rhodopsin for up to 24 hours.

* * * * *